US007476397B2

(12) United States Patent
Bessette et al.

(10) Patent No.: US 7,476,397 B2
(45) Date of Patent: Jan. 13, 2009

(54) SYNERGISTIC AND RESIDUAL PESTICIDAL COMPOSITIONS CONTAINING PLANT ESSENTIAL OILS

(75) Inventors: Steven M. Bessette, Brentwood, TN (US); Myron A. Beigler, Santa Rosa, CA (US)

(73) Assignee: EcoSmart Technologies, Inc., Alpharetta, GA (US)

( * ) Notice: Subject to any disclaimer, the term of this patent is extended or adjusted under 35 U.S.C. 154(b) by 0 days.

(21) Appl. No.: 11/046,231

(22) Filed: Jan. 31, 2005

(65) Prior Publication Data

US 2005/0260241 A1      Nov. 24, 2005

Related U.S. Application Data

(62) Division of application No. 09/362,189, filed on Jul. 28, 1999, now Pat. No. 6,849,614.

(60) Provisional application No. 60/122,803, filed on Mar. 3, 1999, provisional application No. 60/100,613, filed on Sep. 16, 1998, provisional application No. 60/094,463, filed on Jul. 28, 1998.

(51) Int. Cl.
  *A01N 25/32*  (2006.01)

(52) U.S. Cl. .................. 424/406; 424/764; 514/63; 514/65; 514/72; 514/731

(58) Field of Classification Search .................. 424/406
See application file for complete search history.

(56) References Cited

U.S. PATENT DOCUMENTS

| 2,144,366 | A | * | 1/1939 | Faloon | .................. 514/72 |
|---|---|---|---|---|---|
| 2,945,782 | A |  | 7/1960 | Schraufstatter et al. | |
| 3,445,565 | A |  | 5/1969 | Locher et al. | |
| 4,368,207 | A |  | 1/1983 | Lover et al. | |
| 4,663,315 | A |  | 5/1987 | Hasegawa et al. | |
| 4,759,930 | A |  | 7/1988 | Granirer et al. | |
| 4,933,371 | A |  | 6/1990 | Hink et al. | |
| 5,412,958 | A |  | 5/1995 | Iliff et al. | |
| 5,776,477 | A |  | 7/1998 | Ryder et al. | |
| 2008/0015167 | A1 |  | 1/2008 | Bessette et al. | |

FOREIGN PATENT DOCUMENTS

| BE | 906 136 A | 4/1987 |
|---|---|---|
| BE | 1 002 598 A6 | 4/1991 |
| BE | 1002598 | 4/1991 |
| CN | 1 087 228 A | 6/1994 |
| DE | 4421471 | 1/1969 |
| DE | 37 17 467 A1 | 12/1988 |
| DE | 37 33 640 A1 | 4/1989 |
| DE | 3733640 | 4/1989 |
| EP | 0262885 | 4/1988 |
| FR | 1 397 600 A | 4/1965 |
| FR | 2 071 322 A | 9/1971 |
| FR | 2071322 | * 9/1971 |
| FR | 2 447 681 A | 8/1980 |
| GB | 1 574 609 A | 9/1980 |
| JP | 55 104202 A | 8/1980 |
| JP | 4-154719 | * 5/1992 |
| JP | 04 154719 A | 5/1992 |
| JP | 05-246801 | 12/1994 |
| WO | WO 8505038 | 11/1985 |
| WO | WO 9108670 | 6/1991 |
| WO | WO 95/11205 | 4/1995 |
| WO | WO 9854971 | 4/1998 |
| WO | WO 9918802 | 10/1998 |

OTHER PUBLICATIONS

JPAB abstract of JP 04154719 May 27, 1992.*
Eldoksch, Hamdy et al, "Toxicity and synergism of some patent extracts and insecticides against European corn borer egg-masses", Chemical Abstracts, 124(19), May 6, 1996.
Casida, John E., Pyrethrum, The Natural Insecticide, p. 30-32, 196,197 (1973).
Laurent et al., "Insecticidal Activity of Essential Oils on *Triatoma infestans*", *Phytotherapy Research*, vol. 11:285-290 (1997).
Abstract—Bestmann, et al., "Plant insecticides. III. Pyrethrim I in the essential oil of Chrysanthemum balsamita L", *Journal of Biosciences*, 41(7-8):725-728 (1986) Chemical Abstracts Service, XP002381363.
Abstract—Laurent et al., "Insecticidal activity of essential oils on Triatoma infestans", *Phytotherapy Research*, 11(4):285-290 (1997) Chemical Abstracts Service, XP002381364.

* cited by examiner

*Primary Examiner*—Neil Levy
(74) *Attorney, Agent, or Firm*—Nixon & Vanderhye P.C.

(57) ABSTRACT

Synergistic and residual pesticidal compositions containing synergistic and residual mixtures of plant essential oils and/or their constituents, plant essential oils and/or their constituents in admixture with known active pesticidal compounds or plant essential oils and/or their constituents in admixture with other compounds not previously used as active ingredients in pesticidal formulations, such as, for example, so called signal transduction modulators. In addition, the present invention is directed to a method for controlling pests by applying a pesticidally effective amount of the above synergistic and residual pesticidal compositions to a locus where pest control is desired.

4 Claims, No Drawings

SYNERGISTIC AND RESIDUAL PESTICIDAL COMPOSITIONS CONTAINING PLANT ESSENTIAL OILS

This application is a divisional of U.S. application Ser. No. 09/362,189, filed Jul. 28, 1999, now U.S. Pat. No. 6,849,614 which claims the benefit of (1) U.S. Provisional Patent Application Ser. No. 60/094,463, filed Jul. 28, 1998; (2) U.S. Provisional Patent Application Ser. No. 60/100,613, filed Sep. 16, 1998; and (3) U.S. Provisional Patent Application Ser. No. 60/122,803, filed Mar. 3, 1999, the entire disclosures of which are incorporated herein by reference.

FIELD OF THE INVENTION

The present invention relates, in general, to pesticidal compositions and, in particular, synergistic and residual pesticidal compositions containing plant essential oils and/or their constituents. In one aspect, the present invention relates to synergistic pesticidal compositions containing synergistic mixtures of plant essential oils and/or their constituents. In another aspect, the present invention relates to synergistic pesticidal compositions containing certain plant essential oils and/or their constituents in admixture with known active pesticidal compounds. In another aspect, the present invention relates to residual pesticidal compositions containing certain plant essential oils and/or their constituents in admixture with known active pesticidal compounds and other compounds not previously used as active ingredients in pesticidal compositions, such as, for example, so called signal transduction modulators known to have beneficial use in the pharmaceutical arts. In a further aspect, the present invention relates to a method for controlling pests by the application of pesticidally effective amounts of the above synergistic and residual pesticidal compositions to a locus where pest control is desired.

BACKGROUND OF THE INVENTION

Pests (invertebrates, insects, arachnids, mites, larvae thereof, etc.) are annoying to humans for a myriad of reasons. They have annually cost humans billions of dollars in crop losses and in the expense of keeping them under control. For example, the losses caused by pests in agricultural environments include decreased crop yield, reduced crop quality, and increased harvesting costs.

Over the years, synthetic chemical pesticides have provided an effective means of pest control. For example, one prior approach involves the use of complex, organic insecticides, such as those disclosed in U.S. Pat. Nos. 4,376,784 and 4,308,279. Other prior approaches employ absorbent organic polymers for widespread dehydration of the insects. See, U.S. Pat. Nos. 4,985,251; 4,983,390; 4,818,534; and 4,983,389. Use of inorganic salts as components of pesticides has also been tried, as disclosed in U.S. Pat. Nos. 2,423,284 and 4,948, 013, European Patent Application No. 462 347, Chemical Abstracts 119(5):43357q (1993) and Farm Chemicals Handbook, page c102 (1987).

However, it has become increasingly apparent that the widespread use of synthetic chemical pesticides has caused detrimental environmental effects that are harmful to humans and other animals. For instance, the public has become concerned about the amount of residual chemicals that persist in food, ground water and the environment, and that are toxic, carcinogenic or otherwise incompatible to humans, domestic animals and/or fish. Moreover, some target pests have even shown an ability to develop resistance to many commonly used synthetic chemical pesticides. In recent times, regulatory guidelines have encouraged the development of potentially less harmful pesticidal compositions via stringent restrictions on the use of certain synthetic pesticides. As a result, elimination of effective pesticides from the market has limited economical and effective options for controlling pests. As an alternative, botanical pesticides are of great interest because they are natural pesticides, i.e., toxicants derived from plants that are safe to humans and the environment. Historically, botanical pesticides, such as tobacco, pyrethrum, derris, hellebore, quassia, camphor and turpentine, have long been used. Of the botanical pesticides, pyrethrum (also known as caucasian pyrethrum, dalmatic pyrethrum, pesticide chrysanthemum, natural pyrethrum and pyrethrin) has found widespread use.

Pyrethrum, which is extracted from the flowers of a chrysanthemum grown in Kenya and Ecuador, acts on insects with phenomenal speed causing immediate paralysis, while at effective pesticidal concentrations exhibits negligible toxic effects on humans and warm-blooded animals. Use of pyrethrins for industrial or agricultural applications, however, is attendant with several disadvantages. For example, they require frequent treatments because they readily decompose when exposed to direct sunlight. Pyrethrins are also neurotoxic to cold-blooded animals, such as fishes, reptiles, etc. Moreover, the supply of pyrethrins is limited and substantial processing is required to bring the natural product to market, and large-scale production is very expensive. Unless pyrethrins are formulated with a synergist, most initially paralyzed insects recover to once again become pests.

Synergists are compounds that, although typically possessing no direct toxic effect at the dosage employed, are able to substantially enhance the observed toxicity of a pesticide with which they are combined. Synergists are found in most household, livestock and pet aerosols to enhance the action of the fast knockdown pesticides, e.g., pyrethrum, allethrin, and resmethrin, against flying insects. Synergists are required in pesticidal formulations containing pyrethrum, for example, because target insects produce an enzyme (cytochrome P-450) that attacks pyrethrum and breaks it down, thereby making it effective in knocking an insect down, but ineffective for killing in many cases. As such, these synergists act by inhibiting P-450-dependent polysubstrate monooxygenase enzymes (PSMOs) produced by microsomes, which are subcellular units found in the liver of mammals and in some insect tissues that degrade pyrethrum and other pesticidal compounds, such as pyrethrum, allethrin, resmethrin, and the like.

Piperonyl butoxide (PBO) is the main pesticide synergist in commerce. PBO, however, is a synthetic product that has recently been scrutinized by regulatory agencies and certain other groups. As a result, the industry has turned to synthetic pyrethroids, which are very photostable in sunlight and are generally effective against most agricultural insect pests. Pyrethroids are not as safe as pyrethrins, however, and disadvantageously persist in the environment for longer periods. Further, many insects disadvantageously develop resistance to pyrethroids.

Many natural products used as insecticides, including plant essential oils, do not provide adequate control of pests in that they are not very stable and break down quickly, thereby failing to provide toxic residual properties. Products such as pyrethrum, although highly toxic to pests on contact when used properly in pesticidal formulations, are not effective pesticides for many applications because they lack residual properties, thereby increasing the frequency and cost of pesticide applications, as well as increased risk and exposure to the environment.

Accordingly, there is a great need for novel synergistic and residual pesticidal compositions containing no level or substantially lower levels of synthetic pyrethroids, chlorinated hydrocarbons, organophosphates, carbamates and the like. In addition, there is a need for methods for using same that address the problems described above, i.e. are safe to humans and the environment and relatively inexpensive to use in obtaining acceptable levels of insect or pest control.

SUMMARY OF THE INVENTION

A primary object of the present invention is to provide novel pesticidal compositions that contain at least one plant essential oil, derivatives thereof, and/or their constituents as a synergist and at least one known conventional pesticidal compound.

Another object of the present invention is to provide pesticidal compositions containing synergistic mixtures or blends of plant essential oils and/or their constituents.

Still another object of the present invention is to provide new uses for signal transduction modulators in pesticidal compositions comprising at least one plant essential oil, derivatives thereof and/or their constituents, and/or conventional pesticides.

A further object of the present invention is to provide pesticidal compositions wherein the active synergistic compositions of the present invention can be employed in a reduced amount and still achieve the desired pest control.

A further object of the present invention is to provide novel, residual pesticidal compositions that contain admixtures of certain compounds, natural or synthetic, with certain plant essential oils and/or their constituents that act to residualize the toxic effects of pesticidal compositions containing the plant essential oils and/or their constituents.

A still further object of the present invention is to provide a method for controlling pest growth by the application of the compositions of the present invention to a locus where such control is desired.

Another object of the present invention is to provide a pesticidal composition and method for mechanically and neurally controlling pests, e.g., invertebrates, insects, arachnids, larvae thereof, etc.

A further object of the present invention is to provide a safe, non-toxic pesticidal composition and method that will not harm the environment.

Another object of the present invention is to provide a pesticidal composition and method that has a pleasant scent and that can be applied without burdensome safety precautions.

Still another object to of the present invention is to provide a pesticidal composition and method as described above which can be inexpensively produced or employed.

Yet another object of the present invention is to provide a pesticidal composition and method to which pests cannot build resistance.

The above and other objects are accomplished by the present invention which is directed to (1) a synergistic and residual pesticidal composition containing at least two plant essential oil, derivatives thereof, and/or their constituents, (2) synergistic and residual pesticidal compositions comprising plant essential oils and/or their constituents in admixture with known active pesticidal compounds, (3) synergistic and residual pesticidal compositions comprising plant essential oils and/or their constituents in admixture with compounds not previously used as active ingredients in pesticidal compounds, e.g., signal transduction modulators (inhibitors and/or activators), or (4) synergistic and residual pesticidal compositions comprising known active pesticidal compounds in admixture with other compounds not previously used as active ingredients in pesticidal compounds, e.g., signal transduction modulators. It will be understood that throughout this description, the meaning of term "signal transduction modulators" shall encompass inhibitors and/or activators. In addition, the present invention is directed to methods for controlling pests by the applying a pesticidally effective amount of the above synergistic and residual pesticidal compositions to a locus where pest control is desired.

Additional objects and attendant advantages of the present invention will be set forth, in part, in the description that follows, or may be learned from practicing or using the present invention. The objects and advantages may be realized and attained by means of the instrumentalities and combinations particularly recited in the appended claims. It is to be understood that the foregoing general description and the following detailed description are exemplary and explanatory only and are not to be viewed as being restrictive of the invention, as claimed.

DETAILED DESCRIPTION OF PREFERRED EMBODIMENTS

All patents, patent applications and literatures cited in this description are incorporated herein by reference in their entirety. In the case of inconsistencies, the present disclosure, including definitions, will prevail.

In one embodiment, the present invention provides a synergistic and residual pesticidal composition comprising, in admixture with a suitable carrier and optionally with a suitable surface active agent, at least two plant essential oil compounds or derivatives thereof, including racemic mixtures, enantiomers, diastereomers, hydrates, salts, solvates, metabolites, analogs, homologs, etc.

Each plant essential oil or derivative thereof, which may be extracted from natural sources or synthetically made, generally contains, as a major constituent, an acyclic monoterpene alcohol or aldehyde, a benzenoid aromatic compound containing at least one oxygenated substituent or side chain, or a monocarbocyclic terpene generally having a six membered ring bearing one or more oxygenated substituents. Examples of such essential oils or their constituents include, but are not limited to, members selected from the group consisting of aldehyde C16 (pure), alpha-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, dimethyl salicylate, eucalyptol (cineole), eugenol, iso-eugenol, galaxolide, geraniol, guaiacol, ionone, d-limonene, menthol, methyl anthranilate, methyl ionone, methyl salicylate, alpha-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil (white and red), thymol, trans-anethole, vanillin, ethyl vanillin, and the like. As these plant essential oil compounds are known and used for other uses, they may be routinely prepared by a skilled artisan by employing known methods.

Further, the present invention provides new uses for so called signal transduction modulators. Signal transduction modulators have been known to show therapeutic utility or potential in the pharmaceutical arts, but have heretofore not been known to exhibit utility in the pesticidal arts. As such, the synergistic and residual pesticidal compositions of the present invention may comprise known active pesticidal compounds and/or at least one of the above plant essential oil compounds, and at least one signal transduction modulator. Preferred signal transduction modulators include those that are effective for the disruption of cyclic adenosine monophosphate (cAMP)/cAMP-dependent protein kinase, tyrosine kinase, MEK 1 or MEK 2, calcium phospholipid-dependent protein kinase (PKC), mitogen activated protein kinase family members, calcium-calmodulin-dependent protein kinase, growth factor receptor, octopamine receptor, etc. Preferred signal transduction modulators include, but are not limited to, forskolin, PD98059 (also known as 2-(2-amino-3-methoxyphenyl)-4-oxo-4H-[1]benzopyran or 2'-amino-3'-methoxy-flavone), geldanamycin, lavendustin A, lavendustin B, lavendustin C, genistein, herbimycin A, 2-hydroxy-5-(2, 5-di-hydroxybenzyl)amino-benzoic acid, methyl 2,5-dihydroxycinnamate, tyrphostin, staurosporine, cytochalasin B, and the like.

In another preferred embodiment, the present invention includes a synergistic pesticidal composition for agricultural use comprising a mixture of eugenol, alpha-terpineol, citronellal, thymol and trans-anethole. Data below shows that trans-anethole synergizes the action of thyme oil and thyme oil derivatives such as thymol and carvacrol, which are believed to antagonize mitochondrial electron transport pathways in pests.

In another preferred embodiment, the present invention is directed to a synergistic pesticidal composition for controlling household pests comprising alpha-terpineol, benzyl alcohol, 2-phenylethyl alcohol and/or 2-phenylethyl propionate. Data below shows that this embodiment is highly effective, i.e., exhibited increased toxicity, against fire ants and cockroaches compared to the individual plant essential oils, alone.

In still another preferred embodiment, the present invention is directed to synergistic and residual pesticidal compositions comprising at least one plant essential oil compound and at least one pesticidal agent selected from the group consisting of a natural insecticide compound, chlorinated hydrocarbon, an organophosphate, a carbamate and the like, in admixture with a suitable carrier and optionally a suitable surface active agent. Preferred pesticidal agents include, without limitation, allethrin, azadirachtin (neem), carbaryl, chlorpyrifos, DDT, fenvalorate, malathion, permethrin, pyrethrum, resmethrin, rotenone, pyrethroids, etc.

In a further preferred embodiment, the present invention encompasses synergistic and residual pesticidal compositions comprising at least one of the above plant essential oil compounds and one or more members selected from the group consisting of pyrethrolone, allethrolone, chrysanthemic acid, chrysanthemyl alcohol, cis-jasmone, and dimethyl sulfoxide (DMSO), in admixture with a suitable carrier and optionally a suitable surface active agent.

In another preferred embodiment, the present invention is directed to a synergistic and residual pesticidal composition comprising at least one of the above plant essential oil compounds, a pesticidal agent and a signal tranduction modulator.

It will be appreciated by the skilled artisan that the synergistic and residual pesticidal compositions of the present invention unexpectedly exhibit excellent pesticidal activities at sub-lethal dosage regimens, i.e., using active pesticidal agents at lesser concentrations than the individual compounds. Further, it will be appreciated by the skilled artisan that the synergistic and residual pesticidal compositions of the present invention unexpectedly exhibit pesticidal activity for extended periods of time, (i.e. using natural compounds as residual insecticides that in and of themselves provide little, if any, residual pesticide properties). Without wishing to be bound by the following theories, it is possible that plant essential oils antagonize a pest's nerve receptors or may act as P-450 inhibitors. Alternatively, plant essential oils may act via an alternative mode of action. In the case where pyrethrum is the pesticidal agent in admixture with one or more plant essential oils, it is believed that pyrethrum facilitates penetration of a pest cuticle, thereby increasing access of the plant essential oils to the pest's nerve receptors. Further, another possibility is that pyrethrum and other pesticidal agents biochemically synergize the plant essential oils. The pesticidal agents may also disrupt energy levels within the insect's metabolism, thereby synergizing the antagonistic action of so-called octopamine affectors. In any event, the net effect of the increased toxicity and synergized action of the inventive synergistic composition disclosed herein is heretofore unknown and unexpected.

Use of synergistic and residual pesticidal compositions of the present invention generally results in 100% mortality on contact and provide residual toxic properties for at least two weeks. As such, they are advantageously employed as pesticidal agents in uses such as, without limitation, agriculture, organic farming, households, professional pest control, pet bedding, foliage application, underwater or submerged application, solid treatment, soil incorporation application, seedling box treatment, stalk injection and planting treatment, ornamentals, and against termites, mosquitoes, fire ants, head lice, dust mites, etc.

With respect to plants, the synergistic and residual pesticidal compositions resist weathering which includes wash-off caused by rain, decomposition by ultra-violet light, oxidation, or hydrolysis in the presence of moisture or, at least such decomposition, oxidation and hydrolysis as would materially decrease the desirable pesticidal characteristic of the synergistic and residual compositions or impart undesirable characteristics to the synergistic and residual compositions. The synergistic and residual compositions are so chemically inert that they are compatible with substantially any other constituents of the spray schedule, and they may be used in the soil, upon the seeds, or the roots of plants without injuring either the seeds or roots of plants. They may also be used in combination with other pesticidally active compounds.

The term "carrier" as used herein means a material, which may be inorganic or organic and of synthetic or natural origin, with which the active compound is mixed or formulated to facilitate its application to the plant, seed, soil or other object to be treated, or its storage, transport and/or handling. In general, any material that may be customarily employed as a carrier in insecticidal, herbicidal, or fungicidal formulations, are suitable for use with the present invention. The inventive synergistic and residual pesticidal compositions of the present invention may be employed alone or in the form of mixtures with such solid and/or liquid dispersible carrier vehicles and/or other known compatible active agents, especially plant protection agents, such as other insecticides, acaricides, miticides, nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. The synergistic and residual pesticidal compositions of the present invention can be formulated or mixed with, if desired, conventional inert (i.e. plant compatible or herbicidally inert) pesticide diluents or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc.

Formulations containing the synergistic and residual compositions of the present invention may be prepared in any known manner, for instance by extending the synergistic and residual compositions with conventional pesticide dispersible liquid carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. Suitable liquid diluents or carriers include water, petroleum distillates, or other liquid carriers with or without surface active agents. The choice of dispersing and emulsifying agents and the amount employed is dictated by the nature of the composition and the ability of the agent to facilitate the dispersion of the synergistic and residual compositions of the present invention. Generally, it is desirable to use as little of the agent as is possible, consistent with the desired dispersion of the synergistic and residual compositions of the present invention in the spray so that rain, dew, fog, etc. does not re-emulsify the synergistic and residual compositions of the present invention after it is applied to the plant and wash it off the plant. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

Liquid concentrates may be prepared by dissolving a composition of the present invention with a non-phytotoxic solvent and dispersing the synergistic and residual compositions of the present inventions in water with suitable surface active emulsifying and dispersing agents. Examples of conventional carrier vehicles for this purpose include, but are not limited to, aerosol propellants which are gaseous at normal temperatures and pressures, such as Freon; inert dispersible liquid diluent carriers, including inert organic solvents, such as aromatic hydrocarbons, e.g. benzene, toluene, xylene, alkyl naphthalenes, etc., halogenated especially chlorinated, aromatic hydrocarbons, e.g. chloro-benzenes, etc., cycloalkanes, e.g. cyclohexane, etc., paraffins, e.g. petroleum or mineral oil fractions, chlorinated aliphatic hydrocarbons, e.g. methylene chloride, chloroethylenes, etc., alcohols, e.g. methanol, ethanol, propanol, butanol, glycol, etc., as well as ethers and esters thereof, e.g. glycol monomethyl ether, etc., amines, e.g. ethanolamine, etc., amides, e.g. dimethyl formamide etc., sulfoxides, e.g. dimethyl sulfoxide, etc., acetonitrile, ketones, e.g. acetone, methyl ethyl ketone, methyl isobutyl ketone, cyclohexanone, etc., and/or water, as well as inert dispersible finely divided solid carriers such as ground natural minerals, e.g. kaolins, clays, vermiculite, alumina, silica, chalk, i.e. calcium carbonate, talc, attapulgite, montmorillonite, kieselguhr, etc., and ground synthetic minerals, e.g. highly dispersed silicic acid, silicates, e.g. alkali silicates, etc.

Surface-active agents, i.e., conventional carrier vehicle assistants, that may be employed with the present invention include, without limitation, emulsifying agents, such as non-ionic and/or anionic emulsifying agents, e.g. sodium dodecyl benzene sulfonate, polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers, magnesium stearate, sodium oleate, etc.

In accordance with the principles of the present invention, insecticides can also be prepared as either water or oil based suspensions. Known quantities of the active materials can be dispersed into water or oil using high speed agitation as delivered from machines such as colloid mills, waring blenders, high speed homogenizers or lightening mixers. These systems are capable of imparting a large amount of energy into the liquid resulting in the generation of very small drops of one liquid dispersed throughout the other. If water is the continuous phase, it is a water-based suspension. If the continuous phase is oil, it is an oil based suspension. To aid in the dispersion of the one fluid into another, emulsifiers and dispersants may be added. These agents can be non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers). To stabilize the mixture, to prevent the agglomeration of the droplets over time, the viscosity of the liquid is adjusted using agents such as xantham gums, polyacryamides or polyacrylates, and swelling clays such as attapulgite, bentonite or veegum. The preferred particle size of the suspended particles is the 3 to 5 micron range. Concentrations of the active may range from 0.01 to 70% with the typical concentration approximately 1 to 50% w/w.

In the preparation of wettable powders, dust or granulated formulations, the active ingredient is dispersed in and on an appropriately divided carrier. In the formulation of the wettable powders the aforementioned dispersing agents as well as lignosulfonates can be included. Dusts are admixtures of the compositions with finely divided solids such as talc, amorphous or fumed silica, attapulgite clay, kaolin, kieselguhr, pyrophyllite, chalk, diatomaceous earths, vermiculite, calcium phosphates, calcium and magnesium carbonates, sulfur, flours, and other organic and inorganic solids which acts carriers for the pesticide. These finely divided solids preferably have an average particle size of less than about 50 microns. A typical dust formulation useful for controlling insects contains 1 part of synergistic and residual composition and 99 parts of diatomaceous earth or vermiculite. Granules may comprise porous or nonporous particles. The granule particles are relatively large, a diameter of about 400-2500 microns typically. The particles are either impregnated or coated with the inventive pesticidal compositions from solution. Granules generally contain 0.05-15%, preferably 0.5-5%, active ingredient as the pesticidally-effective amount. Thus, the contemplated are formulations with solid carriers or diluents such as bentonite, fullers earth, ground natural minerals, such as kaolins, clays, talc, chalk, quartz, attapulgite, montmorillonite or diatomaceous earth, vermiculite, and ground synthetic minerals, such as highly-dispersed silicic acid, alumina and silicates, crushed and fractionated natural rocks such as calcite, marble, pumice, sepiolite and dolomite, as well as synthetic granules of inorganic and organic meals, and granules of organic materials such as peanut shell, paper waste, sawdust, coconut shells, corn cobs and tobacco stalks. Adhesives, such as carboxymethyl cellulose, natural and synthetic polymers, (such as gum arabic, polyvinyl alcohol and polyvinyl acetate), and the like, may also be used in the formulations in the form of powders, granules or emulsifiable concentrations.

If desired, colorants such as inorganic pigments, for example, iron oxide, titanium oxide and Prussian Blue, and organic dyestuffs, such as alizarin dyestuffs, azo dyestuffs or metal phthalocyanine dyestuffs, and trace elements, such as salts of iron, manganese, boron, copper, cobalt, molybdenum and zinc may be used.

If desired, volatile organic compounds suitable as the fragrance ingredient for use in formulations for household or pet applications, include, but are not limited to, amyl salicylate, citronellol, citronelloxyacetaldehyde, cyclamen aldehyde, citronellyl isobutyrate, coumarin, cyclohexyl acetate, cyclohexyl butyrate, diethyl malonate, ethyl 2-acetyl-5-ketohexanoate, isobornyl acetate, linalool, phenethyl alcohol, undecanol, alpha-hexylcinnamaldehyde, 2-methylhexanol, hexalon, phenylacetaldehyde, cis-3-hexen-1-ol, cyclamal, veronol, eugenol, Lyral, Galaxolide, Citralva, musk ambrette, terpinyl acetate, geraniol, alpha-damascone, alpha-methylionone, and the like. Illustrative of volatile essential oils are oil of Bergamot, cedar leaf, cedar wood, geranium, lavender, white cedar, sandalwood oil, rose extract, violet extract, galbanum oil, and the like. Synthetic types of organic fragrances are described in publications such as U.S. Pat. Nos. 4,314,915; 4,411,829; and 4,434,306.

In commercial or agricultural applications, the present invention encompasses carrier composition mixtures in which the synergistic and residual compositions are present in an amount substantially between about 0.01-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates over-all formulations that comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The synergistic and residual compositions can also be used in accordance with so-called ultra-low-volume process, i.e. by applying such compounds or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed. In this process it is possible to use highly concentrated liquid compositions with said liquid carrier vehicles containing from about 20 to 95% by weight of the synergistic and residual compositions or even the 100% active substances alone, e.g. about 20-100% by weight of the synergistic and residual compositions. The mixture of active materials may be applied, without limitation, in sufficient amounts so as to provide about 0.2 to 2 and preferably about 0.5 to 1.5 pounds of active materials per acre. Moreover, the required amount of the synergistic and residual composition contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95% by weight and in the solid formulations from about 0.5 to 90% by weight. Satisfactory sprays, dusts, or granules for general use contain from about ¼ to 15 pounds of active synergistic and residual compositions per acre.

Furthermore, the present invention encompasses methods for killing, combating or controlling pests, which comprises applying to at least one of correspondingly (a) such pests and (b) the corresponding habitat thereof, i.e. the locus to be protected, e.g. to a growing crop, to an area where a crop is to be grown or to a domestic animal, a correspondingly combative, a pesticidally effective amount, or toxic amount of the particular synergistic and residual compositions of the invention alone or together with a carrier as noted above, The instant formulations or compositions may be applied in any suitable usual manner, for instance by spraying, atomizing, vaporizing, scattering, dusting, watering, squirting, sprinkling, pouring, fumigating, and the like. The method for controlling insects comprises applying the inventive composition, ordinarily in a formulation of one of the aforementioned types, to a locus or area to be protected from the insects, such as the foliage and/or the fruit of plants. The compound, of course, is applied in an amount sufficient to effect the desired action. This dosage is dependent upon many factors, including the targeted pest, the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of this invention at the locus to be protected—i.e., the dosage with which the pest comes in contact—is of the order of 0.001 to 0.5% based on the total weight of the formulation being applied, though under some circumstances the effective concentration will be as little as 0.0001% or as much as 20%, on the same basis.

The synergistic and residual pesticidal compositions and methods of the present invention are effective against a wide variety of pests and it will be understood that the pests exemplified and evaluated in the working Examples herein is representative of such a wider variety. For instance, the present invention can be used to control pests that attack plants or warm-blooded animals, stored products and fabrics. Representative crop plants that can be so treated include, without limitation, cotton, corn, deciduous and citrus fruits, tomatoes, maize, ornamental plants, potatoes, rice, soybean, sugar beets, tobacco, wheat, etc. Representative animals that can be protected or treated by the present invention include, without limitation, humans, horses, dogs, cats, cattle, sheep, goats, hogs, etc. Representative stored products that can be protected from pest attack by the present invention include, without limitation, grains, flour and flour products, tobacco and tobacco products, processed foods and the like. Representative fabrics that can be protected from pest attack by the invention are wool, cotton, silk, linen and the like.

The composition and method of the present invention will be further illustrated in the following, non-limiting Examples. The Examples are illustrative of various embodiments only and do not limit the claimed invention regarding the materials, conditions, weight ratios, process parameters and the like recited herein.

EXAMPLE 1

Synergistic Effect of Plant Essential Oils and/or their Constituents with Pyrethrum on the American Cockroach Glass jars were treated with different concentrations of test chemicals in acetone. The acetone was allowed to evaporate and the cockroaches were exposed to the jars. Ten cockroaches were used for each cross-walk treatment. Each individual component, with the exception of pyrethrum, was used at 100 mg/jar. In the co-treatment experiment without pyrethrum, each chemical was used at 20 mg/jar. In the cotreatment experiment with pyrethrum (25% pure pyrethrins), each plant essential oil was used at 20 mg/jar. Pyrethrum was used at 2 mg/jar. Results are shown below.

| Treatment | % Mortality | | |
|---|---|---|---|
| | 24 hrs. | 48 hrs. | 72 hrs. |
| Control | 0 | 0 | 0 |
| 1 – phenylethyl alcohol (100 mg) | 0 | 0 | 10 |
| 2 – α-Terpineol (100 mg) | 20 | 30 | 60 |
| 3 – benzyl alcohol (100 mg) | 0 | 20 | 40 |
| 4 – phenylethyl propionate (100 mg) | 100 | | |
| 5 – eugenol (100 mg) | 100 | | |
| 6 – pyrethrum (55% pure) (2 mg/jar) | 0 | 0 | 10 |
| 1 + 2 + 3 (20 mg each) | 40 | 70 | 80 |
| 1 + 2 + 3 + 4 (20 mg each) | 60 | 100 | |
| 1 + 2 + 3 + 4 + 5 (20 mg each) | 100 | | |
| 1 + pyrethrum (20 mg + 2 mg) | 0 | 20 | 20 |
| 2 + pyrethrum (20 mg + 2 mg) | 40 | 60 | 100 |
| 3 + pyrethrum (20 mg + 2 mg) | 20 | 40 | 80 |
| 4 + pyrethrum (20 mg + 2 mg) | 100 | | |
| 5 + pyrethrum (20 mg + 2 mg) | 100 | | |

EXAMPLE 2

Synergistic Effects of Plant Essential Oils and/or their Constituents with Pyrethrum on the American Cockroach Glass jars were treated with different concentrations of test chemicals in acetone. The acetone was allowed to evaporate and the cockroaches were exposed to the jars. Five cockroaches were used for each cross-walk treatment, with two replicates/treatment. This experiment was repeated 3 times. In the cotreatment experiment with pyrethrum, ten mg/jar of plant essential oils and/or their constituents were used. Pyrethrum was used at one mg/jar in all tests. Results are shown below.

| Treatment | % Mortality at 24 hrs. |
|---|---|
| Control | 0 |
| 1 – Thymol (20 mg/jar) | 0 |
| 2 – Thyme Oil (20 mg/jar) | 0 |
| 3 – Blend 5 (20 mg/jar) | 0 |
| 4 – Eugenol (20 mg/jar) | 0 |
| 5 – Pyrethrum (1 mg/jar) | 0 |
| 1 (10 mg/jar) + pyrethrum | 50 |
| 2 (10 mg/jar) + pyrethrum | 70 |
| 3 (10 mg/jar) + pyrethrum | 80 |
| 4 (10 mg/jar) + pyrethrum | 100 |

The tested dose of Thyme oil, Thymol and Blend 5 did not induce any death or sign of toxicity (body weight and appetite) against female rats (8-10 week-old rat) up to 5 days after treatment. The Blend-5 is a combination of plant essential oils consisting of thymol, eugenol, trans-anethole, alpha-terpineol, and citronellal.

Examples 1 and 2. These Examples show synergistic activity of a synergistic composition containing plant essential oils and/or their constituents and pyrethrum (25% pure pyrethrins) at lesser concentrations, i.e., each at sub lethal dosages.

EXAMPLE 3

Synergistic and Residual Effects of Mixture of Plant Essential Oil(s) with Pyrethrum and Pyrethrum Derivatives Against American Cockroach Glass jars were treated with different concentrations of test chemicals in acetone. The acetone was allowed to evaporate and the cockroaches were exposed to the jars. Five cockroaches were used for each cross-walk treatment, with two replicates/treatment. This experiment was repeated 2 times. The averaged results are shown below.

| Treatment | % Mortality at time interval in days after treatment | | | | | | | | |
|---|---|---|---|---|---|---|---|---|---|
| | 1 hr. | 3 | 5 | 7 | 10 | 20 | 30 | 45 | 60 |
| Control | 0 | 0 | 0 | 0 | 0 | 0 | 0 | 0 | 0 |
| Thymol (30 mg/jar) | 30 | 10 | 0 | | | | | | |
| C-Alcohol (3 mg/jar) + C-Acid (3 mg/jar) | 0 | 0 | 0 | | | | | | |
| Pyrethrum (45% pure) (.3 mg/jar) | 0 | 0 | 0 | | | | | | |
| Thymol (30 mg) + Pyrethrum (.3 mg) | 100 | 100 | 100 | 100 | 100 | 100 | 100 | 80 | 100 |
| Thymol + C-Alcohol + C-Acid (30 mg) + (3 mg) + (3 mg) | 100 | 100 | 100 | 100 | 100 | 80 | 80 | 80 | 70 |
| 4-Blend (25 mg) (phenethyl alcohol, phenethyl propionate, benzyl alcohol, α-terpineol) | 40 | 40 | 10 | 0 | | | | | |
| 4-Blend (25 mg) + pyrethrum (.3 mg) | 100 | 100 | 100 | 100 | 80 | 80 | 60 | 40 | 0 |

The data above demonstrate the synergistic and residual effects of one or more plant essential oils with pyrethrum. The increased toxicity and increased residual action of the synergistic blends are unexpected and provide distinct benefits over existing pesticide technologies.

EXAMPLE 4

Synergistic and Residual Effects of Thymol with Pyrethrum

Glass jars were treated with different concentrations of test chemicals in acetone. The acetone was allowed to evaporate and the cockroaches were exposed to the jars. Five cockroaches were used for each cross-walk treatment, with two replicates/treatment. This experiment was repeated 2 times. Results are shown below.

| Treatment | % Mortality at time interval in days after treatment | | | | |
|---|---|---|---|---|---|
| | 1 hr. | 3 | 10 | 30 | 45 |
| Control | 0 | 0 | 0 | 0 | 0 |
| Thymol (30 mg/jar) | 30 | 10 | 0 | | |
| Thymol (10 mg/jar) | 10 | 0 | 0 | | |
| Thymol (5 mg/jar) | 0 | 0 | 0 | | |
| Pyrethrum (25% pure) (1 mg/jar) | 10 | 10 | 0 | | |
| Pyrethrum (25% pure) (0.3 mg/jar) | 0 | 0 | | | |
| Pyrethrum (25% pure) (0.1 mg/jar) | 0 | 0 | | | |
| Thymol (30 mg) + Pyrethrum (1 mg) | 100 | 100 | 100 | 100 | 80 |
| Thymol (30 mg) + Pyrethrum (0.3 mg) | 100 | 100 | 100 | 100 | 80 |
| Thymol (30 mg) + Pyrethrum (0.1 mg) | 100 | 100 | 100 | 100 | 50 |
| Thymol (10 mg) + Pyrethrum (1 mg) | 100 | 100 | 100 | 100 | 50 |
| Thymol (10 mg) + Pyrethrum (0.3 mg) | 100 | 100 | 100 | 100 | 50 |
| Thymol (10 mg) + Pyrethrum (0.1 mg) | 100 | 100 | 100 | 100 | 20 |
| Thymol (5 mg) + Pyrethrum (1 mg) | 100 | 100 | 100 | 100 | 10 |
| Thymol (5 mg) + Pyrethrum (0.3 mg) | 100 | 100 | 100 | 90 | 0 |
| Thymol (5 mg) + Pyrethrum (0.1 mg) | 100 | 100 | 70 | 40 | 0 |

These data demonstrate the definite synergy and increased residual toxicity of thymol and sublethal amounts of pyrethrum. This synergy and increased residual action at such low levels is unexpected and significant.

EXAMPLE 5

Synergistic and Residual Effect of Mixture of Plant Essential Oil Constituents with Pyrethrins and DMSO A sample of pyrethrins in an acetone solution at a ratio of 1 part pyrethrins to 100 parts acetone was prepared. A second sample containing four plant essential oil constituents (alpha-terpineol, benzyl alcohol, phenyl ethyl alcohol and phenyl ethyl propionate) in equal proportions by weight was prepared. Then, the first and second samples were combined in a 1:1 ratio to obtain a synergized 4-blend composition, 1 part 4-blend to 0.01 parts pyrethrins. The synergized 4-blend composition was then applied to uncovered 9 cm glass petri dishes at 100 ul each. The second sample was applied to uncovered 9 cm glass petri dishes at 500 ul each. After exposure for one hour, allowing the acetone to evaporate, ten fire ants were placed in each petri dish and observed to determine the time to accomplish LD 90, which is the lethal dose required to kill 90% of the test population.

It was observed that the 100 ul of synergized 4-blend killed three times faster than the 500 ul of 4-blend alone. The 100 ul of synergized 4-blend killed the ants in one minute and fifty seconds whereas the 500 ul of 4-blend alone killed the ants in four minutes and forty-five seconds. The ants exposed to the 4-blend composition exhibited increased signs of neurotoxic effect, including tremors and lack of coordination. This data shows that the level of the insecticidal plant essential oils in the synergistic compositions of the present invention may be decreased to lower levels of active ingredient in suitable end-use formulations from 5% to 1%, adding 0.01% pyrethrins, to achieve a faster knockdown and kill, at less cost. Moreover, the synergized sample continued to provide faster residual knockdown and mortality against fire ants than the unsynergized sample for at least fourteen (14) days after exposure. Similar experiments were conducted using dimethyl sulfoxide (DMSO) and it also proved to be synergistic with plant essential oils and the synergized sample also provided residual toxic properties.

EXAMPLE 6

Synergistic and Residual Effects of Thymol with Pyrethrum Derivatives

Glass jars were treated with different concentrations of test chemicals in acetone. The acetone was allowed to evaporate and the cockroaches were exposed to the jars. Five cockroaches were used for each cross-walk treatment, with two replicates/treatment. This experiment was repeated 2 times. Results are shown below.

| Treatment | % Mortality at time interval in days after treatment | | | |
|---|---|---|---|---|
| | 1 hr. | 3 | 10 | 30 |
| Control | 0 | 0 | 0 | 0 |
| Thymol (30 mg/jar) | 50 | 0 | 0 | |
| Chrysanthemate Ester (0.3 mg/jar) | 0 | 0 | 0 | |
| Chrysanthemate Ester (0.6 mg/jar) | 0 | 0 | 0 | |
| Chrysanthemate Ester (3.0 mg/jar) | 20 | 0 | 0 | |
| Thymol (30 mg) + Chrysanthemate Ester (0.3 mg) 100:1 | 0 | 0 | | |
| Thymol (30 mg) + Chrysanthemate Ester (0.6 mg) 50:1 | 0 | 0 | | |
| Thymol (30 mg) + Chrysanthemate Ester (3.0 mg) 10:1 | 100 | 100 | 100 | 100 |

These data demonstrate the definite synergy and increased residual toxicity of thymol and sublethal amounts of pyrethrum derivatives. This synergy and increased residual action at such low levels is unexpected and significant.

EXAMPLE 7

Synergistic and Residual Effects of Mixture of Thymol with Pyrethrum Derivatives and Signal Transduction Modulators Against American Cockroach Glass jars were treated with different concentrations of test chemicals in acetone. The acetone was allowed to evaporate and the cockroaches were exposed to the jars. Five cockroaches were used for each cross-walk treatment, with two replicates/treatment. This experiment was repeated 2 times. Results are shown below.

| Treatment | % Mortality at time interval in days after treatment | | | | | | |
|---|---|---|---|---|---|---|---|
| | 1 hr. | 3 | 5 | 10 | 30 | 45 | 60 |
| Control | 0 | 0 | 0 | 0 | 0 | 0 | 0 |
| Thymol (20 mg/jar) | 10 | 10 | 0 | | | | |
| Cis-Jasmone (3 mg/jar) | 0 | 0 | 0 | | | | |
| PD 98059 (40 ug/jar) | 0 | 0 | 0 | | | | |
| Lavandustin A (40 ug/jar) | 0 | 0 | 0 | | | | |
| Thymol + Cis-Jasmone | 100 | 100 | 100 | 100 | 100 | 100 | 70 |
| Thymol + PD 98059 | 100 | 100 | 100 | 100 | 100 | 100 | 60 |
| Thymol + Lavandustin A | 100 | 100 | 100 | 80 | 100 | 100 | 40 |

The data above demonstrate the synergistic and residual effects of thymol with pyrethrum derivative Cis-Jasmone and signal transduction modulators such as PD 98059 and Lavandustin A. The increased toxicity and increased residual action of the synergistic blends are unexpected and provide distinct benefits over existing pesticide technologies. This data also demonstrates the ratios necessary to produce residual toxic effects.

EXAMPLE 8

Synergistic and Residual Effects of Benzyl Alcohol with Pyrethrum and Other Synergists Glass jars were treated with different concentrations of test chemicals in acetone. The acetone was allowed to evaporate and the cockroaches were exposed to the jars. Five cockroaches were used for each cross-walk treatment, with two replicates/treatment. This experiment was repeated 2 times. Results are shown below.

| Treatment | % Mortality at time interval in days after treatment | | | |
|---|---|---|---|---|
| | 1 hr. | 7 | 30 | 45 |
| Control | 0 | 0 | 0 | 0 |
| Benzyl Alcohol (B-A) (100 mg/jar) | 80 | 0 | 0 | 0 |
| B-A (50 mg/jar) | 0 | 0 | 0 | |
| B-A (50 mg/jar) + Thymol (1 mg) | 100 | 0 | | |
| B-A (50 mg/jar) + Thymol (5 mg) | 100 | 0 | | |
| B-A (50 mg/jar) + Pyrethrum (25% pure) (1 mg) | 100 | 100 | 60 | 0 |
| B-A (50 mg/jar) + Pyrethrum (25% pure) (5 mg) | 100 | 100 | 100 | 30 |
| B-A (50 mg/jar) + Cis-Jasmone (1 mg) | 100 | 0 | 0 | |
| B-A (50 mg/jar) + Chrysanthemyl Alcohol (1 mg) | 100 | 0 | 0 | |
| B-A (50 mg/jar) + Chrysanthemic Acid (1 mg) | 100 | 0 | 0 | |

These data demonstrate the definite synergy and increased residual toxicity of benzyl alcohol with synergists. This synergy and increased residual action at such low levels is unexpected and significant.

EXAMPLE 9

Synergistic and Residual Effects of Benzyl Alcohol with Chrysanthemates

Glass jars were treated with different concentrations of test chemicals in acetone. The acetone was allowed to evaporate and the cockroaches were exposed to the jars. Five cockroaches were used for each cross-walk treatment, with two replicates/treatment. This experiment was repeated 2 times. Results are shown below.

| Treatment | % Mortality at time interval in days after treatment | | | |
|---|---|---|---|---|
| | 1 hr. | 7 | 14 | 21 |
| Control | 0 | 0 | 0 | |
| Benzyl Alcohol (B-A) (100 mg/jar) | 70 | 0 | | |
| Chrysanthemate Ester (C-Ester) (1 mg/jar) | 0 | 0 | | |
| B-A (100 mg/jar) + C-Ester (1 mg) | 100 | 30 | 0 | |
| Chrysanthemyl Alcohol (C-Alcohol) (1 mg) + Chrysanthemic Acid (C-Acid) (1 mg) | 0 | 0 | 0 | |
| B-A (100 mg/jar) + C-Alcohol (1 mg) + C-Acid (1 mg) | 100 | 50 | 0 | |
| C-Ester (10 mg/jar) | 30 | 0 | | |
| B-A (100 mg/jar) + C-Ester (10 mg) | 100 | 100 | 0 | |
| C-Alcohol (10 mg/jar) + C-Acid (10 mg/jar) | 40 | 0 | | |
| B-A (100 mg) + C-Alcohol (10 mg) + C-Acid (10 mg) | 100 | 100 | | |

These data demonstrate the definite synergy and increased residual toxicity of benzyl alcohol with synergists. This synergy and increased residual action at such low levels is unexpected and significant. This data also demonstrates the ratios necessary to produce residual toxic effects.

EXAMPLE 10

Synergistic and Residual Effects of Benzyl Alcohol with Synergists

Glass jars were treated with different concentrations of test chemicals in acetone. The acetone was allowed to evaporate and the cockroaches were exposed to the jars. Five cockroaches were used for each cross-walk treatment, with two replicates/treatment. This experiment was repeated 2 times. Results are shown below.

| Treatment | % Mortality at time interval in days after treatment | | | | | |
|---|---|---|---|---|---|---|
| | 1 hr. | 7 | 14 | 21 | 30 | 45 |
| Control | 0 | 0 | | | | |
| Benzyl Alcohol (B-A) (100 mg/jar) | 70 | 0 | | | | |
| Pulegone (10 ug/jar) | 30 | 20 | | | | |
| Eugenol (10 ug/jar) | 10 | 20 | | | | |
| Cis-Jasmone (10 mg/jar) | 0 | 0 | | | | |
| Tetrahydrofurfuryl Alcohol (THFA) (10 mg/jar) | 0 | 0 | | | | |
| Thymol (15 mg/jar) | 30 | 0 | | | | |
| B-A (100 mg/jar) + Pulegone (10 ug) | 100 | 100 | 0 | | | |
| B-A (100 mg/jar) + Eugenol (10 ug) | 100 | 100 | 20 | 0 | | |
| B-A (100 mg/jar) + Cis-Jasmone (10 mg) | 100 | 100 | 50 | 50 | 40 | 0 |
| B-A (100 mg/jar) + THFA (10 mg) | 100 | 100 | 40 | 50 | 20 | 0 |
| B-A (100 mg/jar) + Thymol (15 mg) | 100 | 100 | 50 | 20 | 0 | 0 |

These data demonstrate the definite synergy and increased residual toxicity of benzyl alcohol with synergists. This synergy and increased residual action at such low levels is unexpected and significant. This data also demonstrates the ratios necessary to produce residual toxic effects.

EXAMPLE 11

Synergistic and Residual Effects of Benzyl Alcohol with Signal Transduction Modulators Glass jars were treated with different concentrations of test chemicals in acetone. The acetone was allowed to evaporate and the cockroaches were exposed to the jars. Five cockroaches were used for each cross-walk treatment, with two replicates/treatment. This experiment was repeated 2 times. Results are shown below.

| Treatment | % Mortality at time interval in days after treatment | | | |
|---|---|---|---|---|
| | 1 hr. | 7 | 14 | 21 |
| Control | 0 | 0 | 0 | |
| Benzyl Alcohol (B-A) (100 mg/jar) | 100 | 0 | 0 | |
| B-A (100 mg/jar) + Lavandustin A (40 ug) | 100 | 100 | 0 | |
| B-A (100 mg/jar) + PD 98059 (40 ug) | 100 | 100 | 0 | |
| B-A (100 mg/jar) + Forskolin (40 ug) | 100 | 100 | 20 | |
| B-A (100 mg/jar) + Geldanamycin (100 ng) | 100 | 80 | 0 | |

These data demonstrate the increased residual toxicity of benzyl alcohol with signal transduction modulators. This synergy and increased residual action at such low levels is unexpected and significant. This data also demonstrates the ratios necessary to produce residual toxic effects.

EXAMPLE 12

Synergistic Effects of Thymol with Conventional Insecticides

Glass jars were treated with different concentrations of test chemicals in acetone. The acetone was allowed to evaporate and the cockroaches were exposed to the jars. Five cockroaches were used for each cross-walk treatment, with two replicates/treatment. This experiment was repeated 2 times. Results are shown below.

| Treatment | % Mortality at time interval in days after treatment | | | |
|---|---|---|---|---|
| | 1 hr. | 7 | 14 | 21 |
| Control | 0 | | | |
| Thymol (10 mg/jar) | 0 | | | |
| Malathion (75 ug/jar) | 0 | | | |
| Deltamethrin (5 ug/jar) | 30 | | | |
| Permethrin (5 ug/jar) | 0 | | | |
| Thymol (10 mg/jar) + Malathion (75 ug/jar) | 0 | | | |
| Thymol (10 mg/jar) + Deltamethrin (5 ug/jar) | 100 | | | |
| Thymol (10 mg/jar) + Permethrin (5 ug/jar) | 0 | | | |

These data demonstrate the synergy of thymol with deltamethrin even at very low levels. This synergy is unexpected and significant.

EXAMPLE 13

Synergistic and Residual Effects of Thymol with Carbaryl

Glass jars were treated with different concentrations of test chemicals in acetone. The acetone was allowed to evaporate and the cockroaches were exposed to the jars. Five cockroaches were used for each cross-walk treatment, with two replicates/treatment. This experiment was repeated 2 times. Results are shown below.

| Treatment | % Mortality at time interval in days after treatment | | | | |
|---|---|---|---|---|---|
| | 1 hr. | 7 | 14 | 21 | 30 |
| Control | 0 | | | | |
| Thymol (15 mg/jar) | 20 | 0 | | | |
| Carbaryl (1.0 mg/jar) | 90 | 20 | 0 | | |
| Carbaryl (0.1 mg/jar) | 30 | 0 | | | |
| Thymol (15 mg/jar) + Carbaryl (1.0 mg/jar) | 100 | 100 | 100 | 100 | 0 |
| Thymol (15 mg/jar) + Carbaryl (0.1 mg/jar) | 100 | 80 | 10 | 0 | |

These data demonstrate the synergy and residual toxicity of thymol with carbaryl even at very low levels. This synergy and residual toxicity is unexpected and significant.

EXAMPLE 14

Synergistic and Residual Effects of Thymol with Conventional Insecticides

Glass jars were treated with different concentrations of test chemicals in acetone. The acetone was allowed to evaporate and the cockroaches were exposed to the jars. Five cockroaches were used for each cross-walk treatment, with two replicates/treatment. This experiment was repeated 2 times. Results are shown below.

| Treatment | % Mortality at time interval in days after treatment | | | | | |
|---|---|---|---|---|---|---|
| | 1 hr. | 7 | 14 | 21 | 30 | 45 |
| Control | 0 | | | | | |
| Thymol (15 mg/jar) | 10 | 20 | 10 | | | |
| Malathion (100 ug/jar) | 100 | 90 | 60 | | | |
| Deltamethrin (5 ug/jar) | 30 | 0 | 0 | | | |
| Permethrin (10 ug/jar) | 10 | 0 | 0 | | | |
| Thymol (15 mg/jar) + Malathion (100 ug/jar) | 40 | 0 | 0 | | | |
| Thymol (15 mg/jar) + Deltamethrin (5 ug/jar) | 100 | 70 | 80 | 100 | 70 | 50 |
| Thymol (15 mg/jar) + Permethrin (10 ug/jar) | 80 | 100 | 90 | 50 | 30 | 0 |

These data demonstrate the synergy and residual toxicity of thymol with deltamethrin and permethrin at very low levels. This synergy and residual toxicity is unexpected and significant. Thymol and malathion are antagonistic.

EXAMPLE 15

Synergistic Effect of Plant Essential Oils and/or their Constituents and Pyrethrum on the American Cockroach This experiment was performed to determine whether pyrethrum (25% pure pyrethrins) act as a synergist to the plant essential oils and/or their constituents or vice versa. Five cockroaches were used for each cross-walk treatment, with two replicates/treatment. This experiment was repeated 2 times. Results are shown below.

| Treatment | % Mortality at 24 hrs. |
|---|---|
| Control | 0 |
| 1 – Thymol (50 mg/jar) | 20 |
| 2 – Thyme Oil (35 mg/jar) | 30 |
| 3 – Blend 5 (40 mg/jar) | 30 |
| 4 – pyrethrum (1 mg/jar) | 0 |
| 1 + pyrethrum | 70 |
| 2 + pyrethrum | 90 |
| 3 + pyrethrum | 100 |

The dose of pyrethrum which did not induce any lethal effects on Am. Cockroaches was mixed as 1 part relative to the test concentration of plant essential oils and/or their constituents. Without wishing to be bound by the following theory, it appears that pyrethrum acts as a synergist to the plant essential oils and their constituents tested. None of the test doses induced any toxicity against female rats.

EXAMPLE 16

Synergistic Toxicity among Plant Essential Oil Constituents

Several experiments were performed to exemplify that binary mixtures of plant essential oil compounds act synergistically. Early $5^{th}$ instar larvae of *Spodoptera litura* (15-20 mg) were treated topically on the dorsum with doses of pure compounds as per standard protocols. Treated larvae were placed on diet in 5 cm plastic petri dishes and mortality observed at 24 hours post-treatment. For each treatment there were four replicates with 10 larvae each. Results are shown below.

| Treatments (µg/larva) | Mortality (%) |
|---|---|
| *Experiment 1* | |
| Acetone control | 0 |
| Thymol (35) | 25 |
| Citronellal (35) | 0 |
| Thymol (35) + citronellal (35) | ND |
| *Experiment 2* | |
| Acetone control | 0 |
| Thymol (40) | 27.5 |
| Thymol (40) + citronellal (40) | 67.5 |
| *Experiment 3* | |
| Acetone control | 0 |
| Thymol (40) | 25 |
| Thymol (40) + citronellal (40) | 57.5 |
| *Experiment 4* | |
| Acetone control | 0 |
| Thymol (40) | 80 |
| Thymol (40) + citronellal (40) | 93.3 |
| *Experiment 5* | |
| Acetone control | 0 |
| Thymol (40) | 20 |
| Thymol (40) + citronellal (40) | 77.5 |
| *Experiment 6* | |
| Thymol (35) | 32.5 |
| α-terpineol (35) | 5 |
| Both at 35 | 32.5 |
| *Experiment 7* | |
| Thymol (35) | 60 |
| Eugenol (35) | 0 |
| Both at 35 | 50 |
| *Experiment 8* | |
| Eugenol (90) | 27.5 |
| α-terpineol (90) | 20 |
| Both at 90 | 35 |
| *Experiment 9* | |
| Citronellal (110) | 10 |
| α-terpineol (110) | 15 |
| Both at 110 | 65 |
| *Experiment 10* | |
| Citronellal (110) | 12.5 |
| Eugenol (110) | 20 |
| Both at 110 | 40 |
| *Experiment 11* | |
| Thymol (35) | 37.5 |
| t-anethole (35) | 12.5 |
| Both at 35 | 100 |
| *Experiment 12* | |
| Thymol (40) | 40 |
| t-anethole (40) | 12.5 |
| Thymol (40) + t-anethole (25) | 97.5 |
| Thymol (40) + t-anethole (20) | 90 |
| Thymol (40) + t-anethole (15) | 87.5 |
| Thymol (40) + t-anethole (10) | 80 |
| Thymol (40) + t-anethole (5) | 70 |
| Thymol (40) + t-anethole (2.2) | 55 |
| *Experiment 13* | |
| t-anethole (60) | 17.5 |
| α-terpineol (60) | 7.5 |
| Both at 60 | 97.5 |
| *Experiment 14* | |
| t-anethole (60) | 30 |
| Eugenol (60) | 8 |
| Both at 60 | 95 |
| *Experiment 15* | |
| t-anethole (70) | 24 |
| Citronellal (70) | 6 |
| Both at 70 | 40 |

Experiments 2-5 show that thymol is synergized by citronellal when applied in equal doses. Experiments 6-10 show that thymol is not synergized by α-terpineol or eugenol. Eugenol does not appear to be synergized by α-terpineol or citronellal. However, α-terpineol and citronellal look to act synergistically (exp. 9). Experiments 11 & 12 show that trans-anethole is a potent synergist for thymol, even at a ratio of 1:8. Experiments 13-15 show that trans-anethole is an effective synergist for eugenol, α-terpineol and citronellal.

EXAMPLE 17

Synergistic Effect of Plant Essential Oils and Propargite Against Two-Spotted Spider Mites Mixtures of 5-Blend (thymol, trans-anethole, α-terpineol, eugenol, and citronellal) with and without the commercial miticide, propargite (Omite™) were tested against adult mites on bean leaf discs. Treatments consisted of spraying adult mites (direct toxicity) and observing for toxicity versus survival. For each treatment there were 5 replicates with 10 mites in each. Mortality was determined. Results are shown below.

|  | % Survival at: | | |
| --- | --- | --- | --- |
| Treatment | 24 hrs. | 48 hrs. | 72 hrs. |
| Control | 4% | 5% | 32% |
| 5-Blend, 0.5% | 0% | 0% | 0% |
| Omite, 0.01% | 5% | 5% | 22% |
| 5-Blend + Omite | 30% | 48% | 52% |

Conclusions: When sprayed directly on adult mites, neither 5-Blend nor Omite are toxic up to 72 hours. However, the combination of the two products shows enhanced toxicity. These data are unexpected and provide advantages over existing pesticide technologies.

EXAMPLE 18

Synergistic Effect of Plant Essential Oils with Conventional Insecticides Against *Spodoptera litura*

Mixtures of 5-Blend (thymol, trans-anethole, α-terpineol, eugenol, and citronellal) with conventional insecticides were tested against 5-day old larvae of *Spodoptera litura* ($2^{nd}$ instar) on cabbage leaf pieces dipped in test solution. Mortality was observed at 24 and 48 hours. For each treatment there were 5 replicates with 50 larvae per replicate (n=250). Results are shown below.

|  | Mortality (%) | |
| --- | --- | --- |
| Treatment | 24 hrs. | 48 hrs. |
| Control | 0 | 0 |
| 5-Blend (1% = 1:100 dilution) | 2 | 6 |
| Tebufenozide (Confirm ™), 0.1 ppm | 4.5 | 41 |
| Cypermethrin (Cymbush ™), 0.01 ppm | 78 | 80 |
| 5-Blend + Tebufenozide | 39 | 74 |
| 5-Blend + Cypermethrin | 58 | 89 |

Conclusions: In this experiment, 5-Blend synergized tebufenozide at 24 hours and 48 hours. The results with cypermethrin are inconclusive due to initial toxicity. These data are unexpected and provide advantages over existing pesticide technologies.

EXAMPLE 19

Synergistic Effect of Plant Essential Oils with Chrysanthemates Against *Spodoptera litura*

Mixtures of 5-Blend (thymol, trans-anethole, α-terpineol, eugenol, and citronellal) and potential synergists were tested by application to cabbage leaf discs dipped in 1% emulsions. There were 4 leaf discs per treatment. Ten 3-day old ($2^{nd}$ instar) *Spodoptera litura* larvae per disc. Potential synergists and insecticides were dissolved in THFA/Tween 20 (carrier/emulsifier) at 10% active ingredient level; mixed with 5-Blend at 1:10 ratio of synergist to 5-Blend. Mortality was observed at 24 and 48 hours. For each treatment there were 5 replicates with 50 larvae per replicate (n=250). Results are shown below.

|  | Mortality (%) | |
| --- | --- | --- |
| Treatment | 24 hrs. | 48 hrs. |
| Control (THFA/Tween 20) | 0 | 0 |
| Cis-Jasmone | 0 | 0 |
| Chrysanthemic Acid | 0 | 0 |
| Chrysanthemyl Alcohol | 0 | 0 |
| Chrysanthemic Esters | 5 | 5 |
| 5-Blend | 20 | 30 |
| 5-Blend + Cis-Jasmone | 60 | 85 |
| 5-Blend + Chrysanthemic Acid | 72.5 | 87.5 |
| 5-Blend + Chrysanthemyl Alcohol | 70 | 87.5 |
| 5-Blend + Chrysanthemic Esters | 60 | 75 |

Conclusions: In this experiment, at a ratio of 10:1, 5-Blend is synergized by cis-jasmone, and the chrysanthemates. There was virtually no damage to the leaf discs in the synergized 5-Blend treatments, 30% damage in the 5-blend alone, and more than 80% in the remaining treatments. The control was completely consumed within 48 hours. These data are unexpected and provide advantages over existing pesticide technologies.

EXAMPLE 20

Synergistic Effect of Benzyl Alcohol with Pyrethrum Against *Spodoptera litura*

Mixtures of 5-Blend and potential synergists were tested by application to cabbage leaf discs dipped in 1% emulsions. There were 4 leaf discs per treatment; ten 3-day old ($2^{nd}$ instar) *Spodoptera litura* larvae per disc. Potential synergists and insecticides were dissolved in THFA/Tween 20 at 10% a.i.; mixed with 5-Blend at 1:10 ratio (synergist:5-Blend). In this example, THFA/Tween 20 at a ratio of 6:1 was used as a carrier/emulsifier for pyrethrum (20% pure pyrethrins) and other test substances. The sample size for each treatment is 40 (4 replicates with 10 insects each) of *Spodoptera litura*. Results are shown below.

| Treatment | Mortality (%) 24 hrs. |
| --- | --- |
| Control (THFA/Tween 20) | 10 |
| Pyrethrum 40:1 (ingredient ratio) | 37.5 |
| Pyrethrum 20:1 | 40 |
| Pyrethrum 10:1 | 100 |
| Benzyl Alcohol | 15 |
| Benzyl Alcohol + Pyrethrum 40:1 | 72.5 |
| Benzyl Alcohol + Pyrethrum 20:1 | 82.5 |
| Benzyl Alcohol + Pyrethrum 10:1 | 100 |

Conclusions: Benzyl alcohol appears to synergize pyrethrum, at least at the lower levels of active ingredient. The effect is obscured at the highest rate because there was 100% mortality with pyrethrum alone. These data are unexpected and provide advantages over existing pesticide technologies.

EXAMPLE 21

Synergistic and Residual Effects of Plant Essential Oils with Conventional Insecticides and Synergists, And Signal Transduction Modulators Glass jars were treated with different concentrations of test chemicals in acetone. The acetone was allowed to evaporate and American cockroaches were exposed to the jars. Five cockroaches were used for each cross-walk treatment, with two replicates/treatment. This experiment was repeated 2 times. Results are shown below.

| Treatment | % Mortality at time interval in days after treatment | | | | |
|---|---|---|---|---|---|
| | 1 hr. | 7 | 14 | 21 | 30 |
| Control | 0 | | | | |
| Benzyl Alcohol (100 mg) | 100 | 0 | 0 | | |
| Mixture ES-2a: | 100 | 100 | 100 | | |
| Benzyl Alcohol (B-A) (100 mg) | | | | | |
| Tetrahydrofurfuryl Alcohol (THFA) (10 mg) | | | | | |
| PD 98059 (100 ug) | | | | | |
| Trans-Anethole (10 mg) | | | | | |
| Pyrethrum (55% pure pyrethrins) (3 mg) | | | | | |
| Mixture ES-2b: | 100 | 100 | 0 | | |
| B-A (100 mg) | | | | | |
| THFA (10 mg) | | | | | |
| PD 98059 (100 ug) | | | | | |
| Trans-Anethole (10 mg) | | | | | |
| Chrysanthemate Ester (5 mg) | | | | | |

These data demonstrate the synergistic and residual toxic effects of plant essential oils with pyrethrum and signal transduction modulators at very low levels. This synergy and residual toxicity is unexpected and significant. Signal transduction modulators may also synergize conventional pesticides and chrysanthemates as it does here with pyrethrum and chrysanthemate ester.

EXAMPLE 22

Synergistic and Residual Effects of Benzyl Alcohol with Trans-Anethole

Glass jars were treated with different concentrations of test chemicals in acetone. The acetone was allowed to evaporate and American cockroaches were exposed to the jars. Five cockroaches were used for each cross-walk treatment, with two replicates/treatment. This experiment was repeated 2 times. Results are shown below.

| Treatment | % Mortality at time interval in days after treatment | | | | |
|---|---|---|---|---|---|
| | 1 hr. | 7 | 14 | 21 | 30 |
| Control | 0 | | | | |
| Benzyl Alcohol (100 mg/jar) | 70 | 0 | | | |
| Trans-Anethole (10 mg/jar) | 0 | | | | |
| Benzyl Alcohol (B-A) (100 mg/jar) with: | | | | | |
| Trans-Anethole 10 mg/jar (1:10) | 100 | 100 | 80 | 40 | 0 |
| Trans-Anethole 2 mg/jar (1:50) | 100 | 0 | | | |
| Trans-Anethole 1 mg/jar (1:100) | 100 | 0 | | | |
| Mixture ES-2b: | 100 | 100 | 0 | | |
| B-A (100 mg) | | | | | |
| THFA (10 mg) | | | | | |
| PD 98059 (100 ug) | | | | | |
| Trans-Anethole (10 mg) | | | | | |
| Chrysanthemate Ester (5 mg) | | | | | |

These data demonstrate the synergistic and residual toxic effects of plant essential oils with pyrethrum and signal transduction modulators at very low levels. This synergy and residual toxicity is unexpected and significant. Signal transduction modulators may also synergize conventional pesticides and chrysanthemates as it does here with pyrethrum and chrysanthemate ester.

EXAMPLE 23

Synergistic and Residual Effects of Thymol with Pyrethrum and Signal Transduction Modulators Glass jars were treated with different concentrations of test chemicals in acetone. The acetone was allowed to evaporate and American cockroaches were exposed to the jars. Five cockroaches were used for each cross-walk treatment, with two replicates/treatment. This experiment was repeated 2 times. Results are shown below.

| Treatment | % Mortality at time interval in days after treatment | | | | | | |
|---|---|---|---|---|---|---|---|
| | 1 hr. | 7 | 14 | 21 | 30 | 45 | 60 |
| Control | 0 | | | | | | |
| Mixture ES-A: | | | | | | | |
| (100 mg thymol + 40 ug PD98059) | | | | | | | |
| 15 minute brief exposure | 100 | 0 | 0 | | | | |
| 24 hour continuous exposure | 100 | 100 | 100 | 60 | 0 | | |
| Mixture ES-B: | | | | | | | |
| (100 mg thymol + 3 mg pyrethrum) | | | | | | | |
| (Pyrethrum = 55% pure pyrethrins) | | | | | | | |
| 15 minute brief exposure | 100 | 100 | 100 | 85 | 85 | 65 | 65 |
| 24 continuous exposure | 100 | 100 | 100 | 100 | 85 | 70 | 80 |
| Mixture ES-C: | | | | | | | |
| (100 mg thymol + 20 mg Phenethyl Propionate + 3 mg Cis-Jasmone) | | | | | | | |
| 15 minute brief exposure | 100 | 0 | | | | | |
| 24 hour continuous exposure | 100 | 100 | 0 | | | | |

After ten minutes of exposure, all roaches from all three products are uncontrolled and unable to walk on the wall of the jars. These data demonstrate the synergistic and residual toxic effects of thymol with other plant essential oils in admixture with pyrethrum and signal transduction modulators at very low levels. This synergy and residual toxicity is unexpected and significant.

EXAMPLE 24

Synergistic Effect of Phenethyl Propionate with Plant Essential Oils and Thymol

In this bioassay, aqueous emulsions (1:400 a.i. to water) of thymol or 5-blend (thymol, trans-anethole, eugenol, α-terpineol, and citronellal) were applied, with and without phenethyl propionate (PEP), to cabbage leaf discs and $3^{rd}$ instar larvae of Spodoptera litura were exposed to the treated discs after drying. There were five replicates with 10 larvae per replicate, and this was repeated two times. Mortality was observed after 24 hours exposure. Results are shown below.

| Treatment | Mortality (%) 24 hrs. |
|---|---|
| Control | 1 |
| 5-Blend | 73 |
| PEP | 8 |
| 5-Blend + PEP (1:1) | 84 |
| Thymol | 98 |
| PEP | 2 |
| Thymol + PEP (1:1) | 84 |

Conclusions: Phenethyl propionate appears to synergize thymol and the 5-Blend. PEP can be used as a diluent for thymol and 5-Blend without appreciable loss of activity. These data are unexpected and provide advantages over existing pesticide technologies.

As can be seen from the above discussion, the synergistic and residual combinations of active compounds according to the present invention are markedly superior to known pesticidal agents/active compounds conventionally used for pest control in the household and in agricultural areas. The pesticidal effectiveness of the particular new synergistic and residual combinations of active compounds of the present invention is substantially (and surprisingly) higher than the sum of the separate effects of the individual active compounds.

Although illustrative embodiments of the invention have been described in detail, it is to be understood that the present invention is not limited to those precise embodiments, and that various changes and modifications can be effected therein by one skilled in the art without departing from the scope and spirit of the invention as defined by the appended claims.

What is claimed is:

1. A pesticidal composition, comprising a pesticidally-acceptable carrier in admixture with a pesticidally-effective amount of a pesticidally-active agent consisting of pyrethrum and thymol with the proviso that no other pesticidally-active ingredient is present, and wherein the ratio of thymol to pyrethrum is from 30:0.1 to 5:1.

2. The pesticidal composition of claim 1, wherein the active agent interferes with neurotransmission in invertebrates.

3. The pesticidal composition of claim 2, wherein the active agent interferes with octopamine receptor sites in invertebrates.

4. A method for killing or controlling invertebrate pests comprising:
   applying an effective amount of the composition of claim 1 to a pest or to a locus where killing or control of invertebrate pests is desired.

* * * * *